(12) United States Patent
Seyler et al.

(10) Patent No.: US 8,667,668 B2
(45) Date of Patent: Mar. 11, 2014

(54) STENT SHEATHING TECHNOLOGY

(75) Inventors: Paul R. Seyler, Flagstaff, AZ (US); Thomas Motsenbocker, Flagstaff, AZ (US); James L. Battaglia, Flagstaff, AZ (US)

(73) Assignee: Machine Solutions, Inc., Flagstaff, AZ (US)

( * ) Notice: Subject to any disclaimer, the term of this patent is extended or adjusted under 35 U.S.C. 154(b) by 1 day.

(21) Appl. No.: 13/506,109

(22) Filed: Mar. 27, 2012

(65) Prior Publication Data

US 2012/0233964 A1 Sep. 20, 2012

Related U.S. Application Data

(62) Division of application No. 11/265,631, filed on Nov. 2, 2005, now Pat. No. 8,141,226.

(60) Provisional application No. 60/624,432, filed on Nov. 2, 2004.

(51) Int. Cl.
  *B21D 39/00* (2006.01)
  *B21D 39/04* (2006.01)
  *B21D 41/00* (2006.01)

(52) U.S. Cl.
  USPC ............... 29/728; 29/283.5; 29/508; 29/715; 72/402

(58) Field of Classification Search
  USPC ........ 29/282, 283.5, 458, 508, 515, 715, 728; 53/203; 72/402, 420; 606/1, 198; 623/1.11, 1.12, 1.15, 1.23
  See application file for complete search history.

(56) References Cited

U.S. PATENT DOCUMENTS

| | | | |
|---|---|---|---|
| 5,814,338 A * | 9/1998 | Veronesi | 424/472 |
| 5,947,993 A | 9/1999 | Morales | |
| 6,063,092 A | 5/2000 | Shin | |
| 6,141,855 A | 11/2000 | Morales | |
| 6,245,100 B1 | 6/2001 | Davila et al. | |
| 6,352,547 B1 * | 3/2002 | Brown et al. | 606/198 |
| 6,360,577 B2 * | 3/2002 | Austin | 72/402 |
| 6,629,350 B2 * | 10/2003 | Motsenbocker | 29/283.5 |
| 6,783,542 B2 | 8/2004 | Eidenschink | |
| 6,991,639 B2 | 1/2006 | Holman et al. | |
| 7,225,518 B2 * | 6/2007 | Eidenschink et al. | 29/283.5 |

(Continued)

FOREIGN PATENT DOCUMENTS

| | | |
|---|---|---|
| EP | 0938877 | 9/1999 |
| EP | 0938877 A2 | 9/1999 |

(Continued)

*Primary Examiner* — Alexander P Taousakis
(74) *Attorney, Agent, or Firm* — Thompson Coburn LLP

(57) ABSTRACT

A method of sheathing a stent including the steps of providing a stent assembly including a catheter member and a stent member disposed about the catheter member; placing a first sheath film adjacent one side of the stent assembly; placing a second sheath film adjacent an opposite side of the stent assembly, and compressing the stent assembly, whereby the first and second sheath films move toward each other and substantially surround the stent assembly. The first and second sheath films are provided in rolls. Compressing is implemented by a radial compression mechanism. The first and second sheath films pass through the radial compression mechanism. Compressing sheaths the stent assembly and crimps the stent onto the catheter. As an alternative to two sheath films, a single film may be used, whereby compressing surrounds the stent assembly with the single sheath film. Also disclosed is an apparatus for sheathing a stent.

10 Claims, 23 Drawing Sheets

(56) References Cited

U.S. PATENT DOCUMENTS

| | | | |
|---|---|---|---|
| 7,587,801 B2 * | 9/2009 | Austin | 29/283.5 |
| 7,681,430 B2 * | 3/2010 | Stenzel | 72/402 |
| 7,765,670 B2 * | 8/2010 | Spencer et al. | 29/451 |
| 7,793,532 B2 * | 9/2010 | Asmus et al. | 72/402 |
| 2002/0161426 A1 | 10/2002 | Iancea | |
| 2004/0199239 A1 | 10/2004 | Austin et al. | |
| 2005/0183259 A1 | 8/2005 | Eidenschink et al. | |

FOREIGN PATENT DOCUMENTS

| | | |
|---|---|---|
| JP | 2001245990 A | 9/2001 |
| WO | 0021464 A1 | 4/2000 |
| WO | WO 00/21464 | 4/2000 |
| WO | 0121110 A1 | 3/2001 |
| WO | WO 01/21110 | 3/2001 |

* cited by examiner

STENT SHEATHING TECHNOLOGY

CROSS-REFERENCE TO RELATED APPLICATIONS, IF ANY

This application claims the benefit under 35 U.S.C. §119(e) of U.S. Non-Provisional patent application Ser. No. 11/265,631, filed Nov. 2, 2005, and which will issue as U.S. Pat. No. 8,141,226 on Mar. 27, 2012, which claims the benefit under 35 U.S.C. §119(e) of Provisional Patent Application Ser. No. 60/624,432, filed Nov. 2, 2004, which is hereby incorporated by reference.

37 C.F.R. §1.71(e) AUTHORIZATION

A portion of the disclosure of this patent document contains material which is subject to copyright protection. The copyright owner has no objection to the facsimile reproduction by anyone of the patent document or the patent disclosure, as it appears in the US Patent and Trademark Office patent file or records, but otherwise reserves all copyright rights whatsoever.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

1. Field of the Invention

The present invention relates, generally, to medical apparatus or devices, processes for making such apparatus, and apparatus for making such apparatus and practicing such processes. Particularly, the invention relates to medical stents, and stent manufacturing processes and apparatus. Most particularly, the invention relates to methods and apparatus for sheathing a stent, and a sheathed stent. Sheathing a stent is useful to protect the stent surface. Sheathing is particularly useful for protecting the stent during crimping or other processing. Sheathing is most particularly useful for crimping relatively sensitive drug coating, polymer, biodegradable, or any material that can be easily damaged from the crimp process stents. This process includes damage caused from low force crimping on soft materials or high force crimping on very hard materials. The apparatus, and manufacturing methods and apparatus therefor may be useful in other areas.

2. Background Information

The state of the art, in general, includes stents (including drug coated stents) and stent making and crimping methods and apparatus. At present, there are a number of problems in crimping coated stents which occur because the coating is typically soft and somewhat fragile. One solution is to place a thin sheath over the stent prior to crimping. The sheath is typically a thin (0.001-0.002 inch) walled tube which is placed by hand over the stent. The assembly is then placed in a crimping apparatus and the assembly is processed as normal. The sheath is then removed from the stent, again by hand, after crimping. This technology is believed to have significant limitations and shortcomings. Hand placement and removal of the sheath is a time consuming and expensive procedure. Also, tubular sheaths are typically expensive and difficult to apply.

For this and other reasons, a need exists for the present invention.

All US patents and patent applications, and all other published documents mentioned anywhere in this application are incorporated by reference in their entirety.

BRIEF SUMMARY OF THE INVENTION

The invention provides a method of sheathing a stent, particularly during a crimping process, and an apparatus for sheathing a stent, in particular during a crimping process, which are practical, reliable, accurate and efficient, and which are believed to fulfil the need and to constitute an improvement over the background technology.

In one aspect, the invention provides a method of sheathing a stent comprising the steps of providing a stent assembly including a catheter member and a stent member disposed about the catheter member; placing a first sheath film adjacent one side of the stent assembly; placing a second sheath film adjacent an opposite side of the stent assembly; and compressing the stent assembly, whereby the first and second sheath films move toward each other and substantially surround the stent assembly.

In an alternative method aspect, the invention provides a method of sheathing a stent comprising the steps of providing a stent assembly; placing a first sheath film having a first edge and a second edge adjacent the stent assembly in a predetermined configuration; and compressing the stent assembly, whereby the sheath film surrounds the stent.

In another aspect, the invention provides an apparatus for sheathing a stent, comprising a crimping mechanism; a sheath film supply; a film feeder for moving at least one film from the film supply through the crimping mechanism, and a stent input system for moving a stent assembly into the crimping mechanism. The sheath film may comprises a single film which is folded to substantially surround the stent assembly or a pair of films which are moved together to substantially surround the stent assembly. Folding or moving the film(s) preferably occurs during actuation of the crimping mechanism.

The features, benefits and objects of the invention will become clear to those skilled in the art by reference to the following description, claim(s), if any, and drawings.

DETAILED DESCRIPTION

Figure 1:
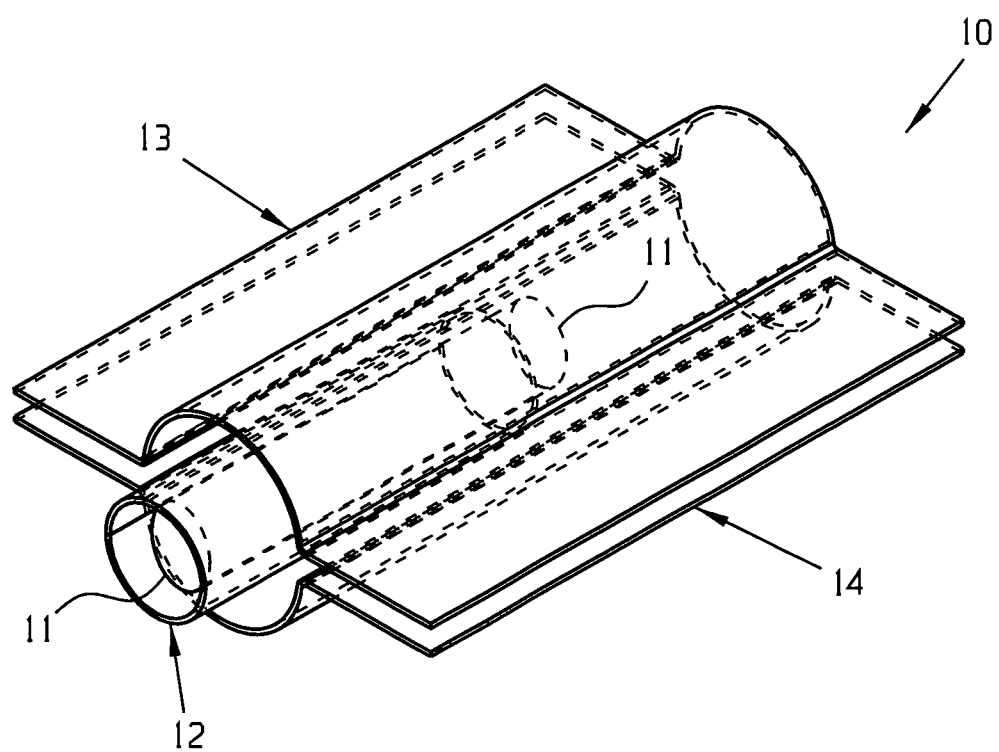
FIG. 1 illustrates an embodiment of the sheathed stent assembly of the present invention.
Figure 2:
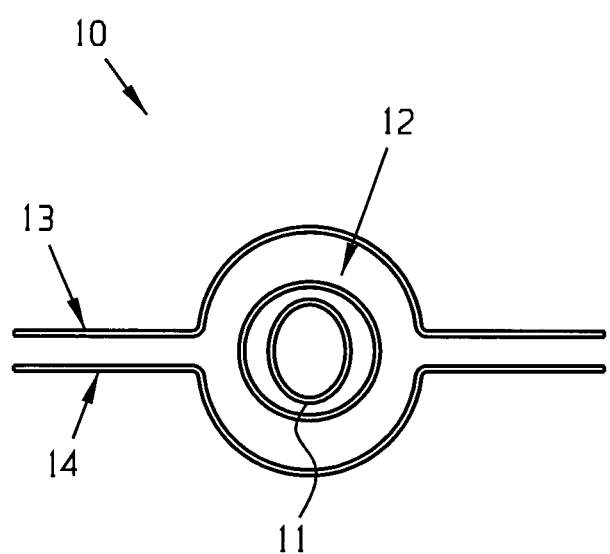
FIG. 2 is an end view of the assembly shown in FIG. 1.
Figure 3:
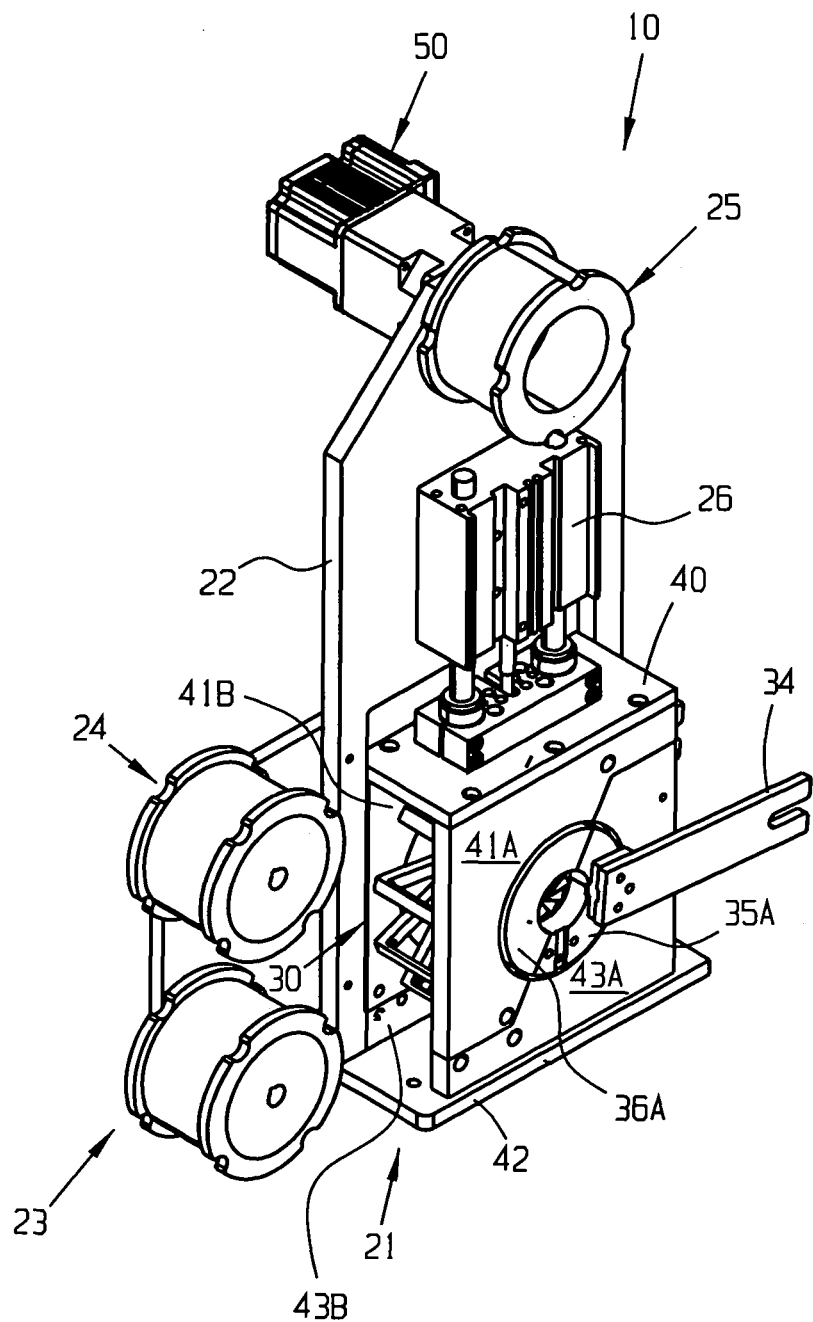
FIG. 3 is a perspective view of an embodiment of an integrated film crimping apparatus of the present invention for sheathing a stent assembly during crimping.
Figure 4:
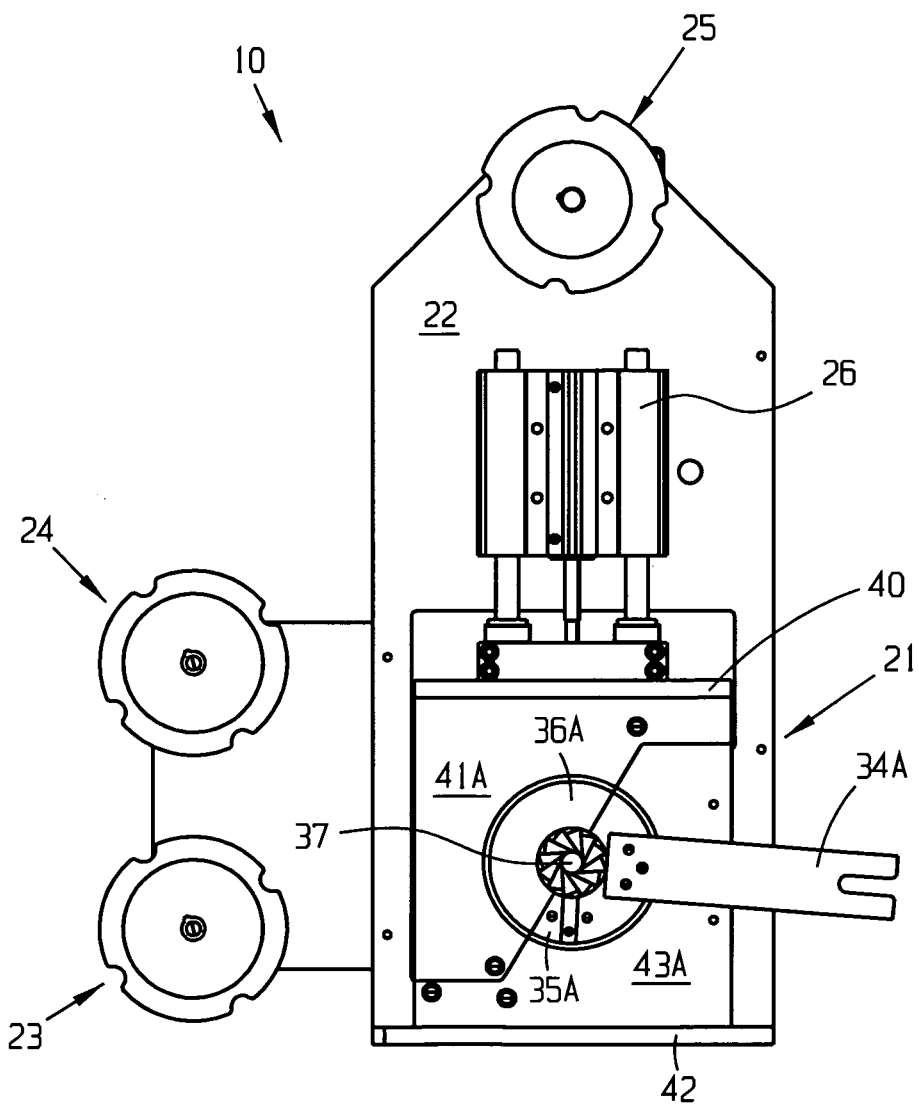
FIG. 4 is a front view of the apparatus.
Figure 5:
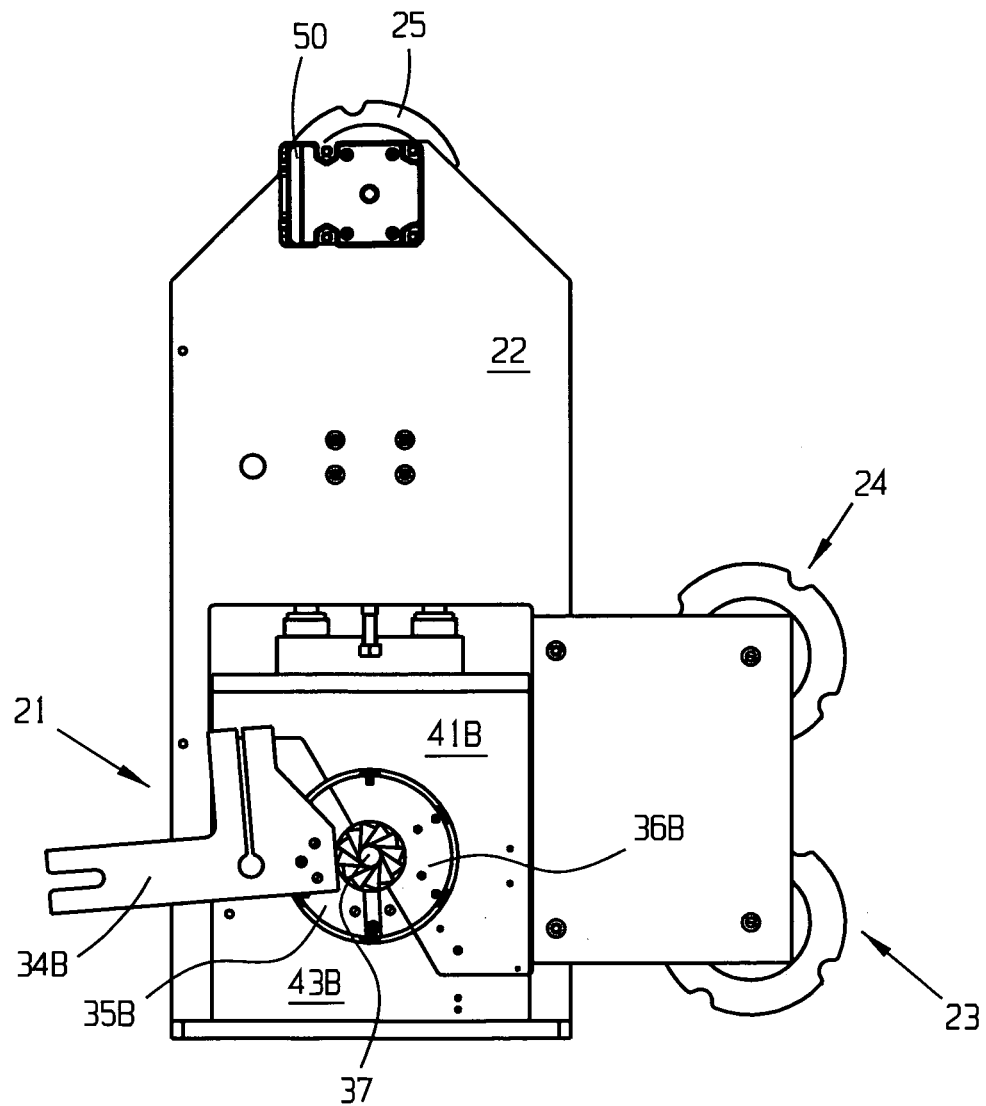
FIG. 5 is a back view of the apparatus.
Figure 6:
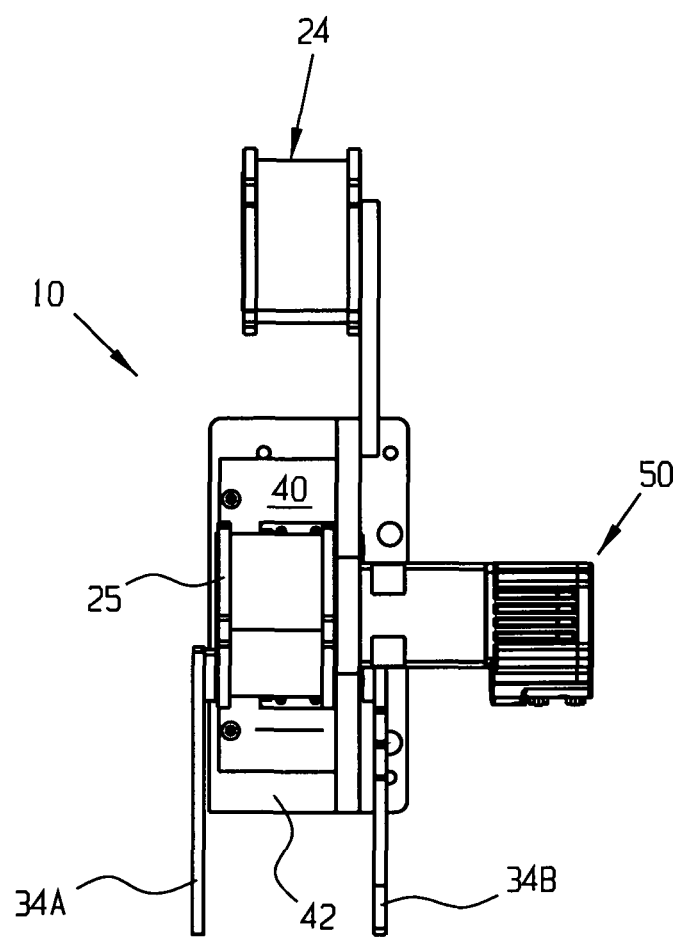
FIG. 6 is a top view of the apparatus.
Figure 7:
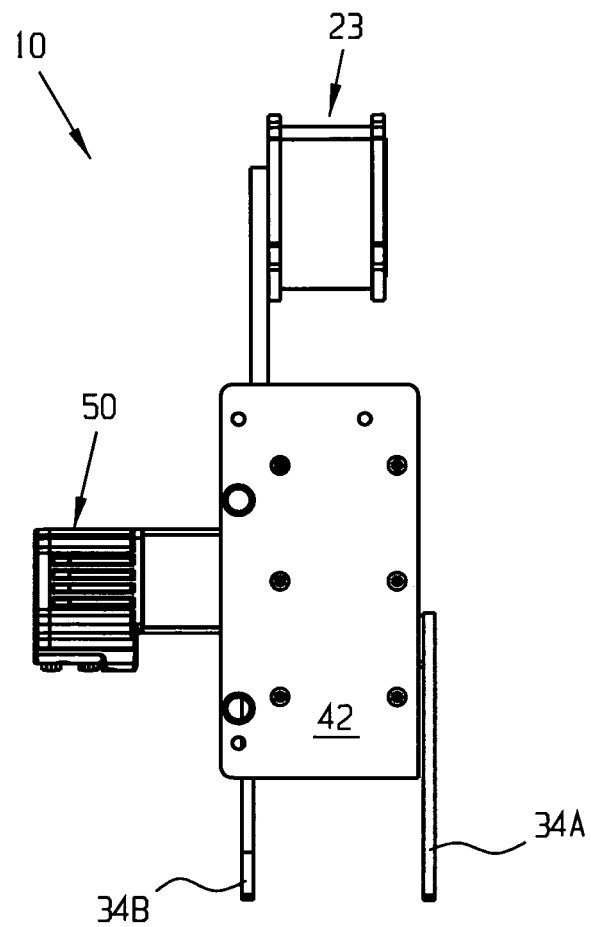
FIG. 7 is a bottom view of the apparatus.
Figure 8:
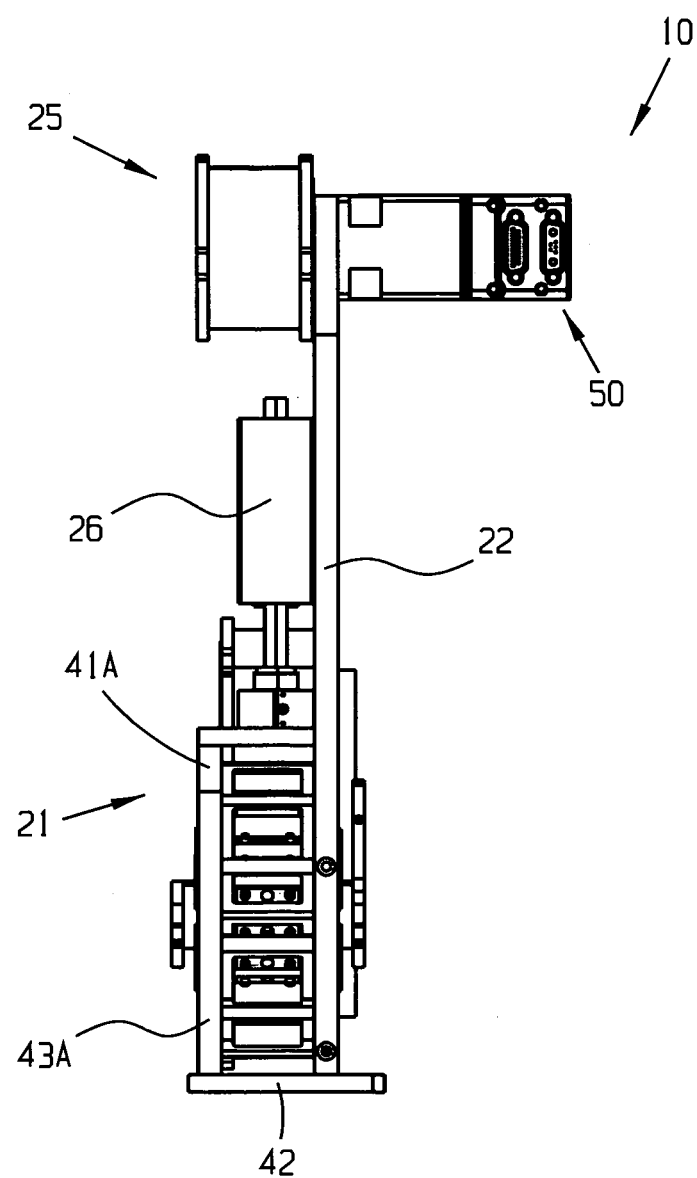
FIG. 8 is a right side view of the apparatus with respect to the front.
Figure 9:
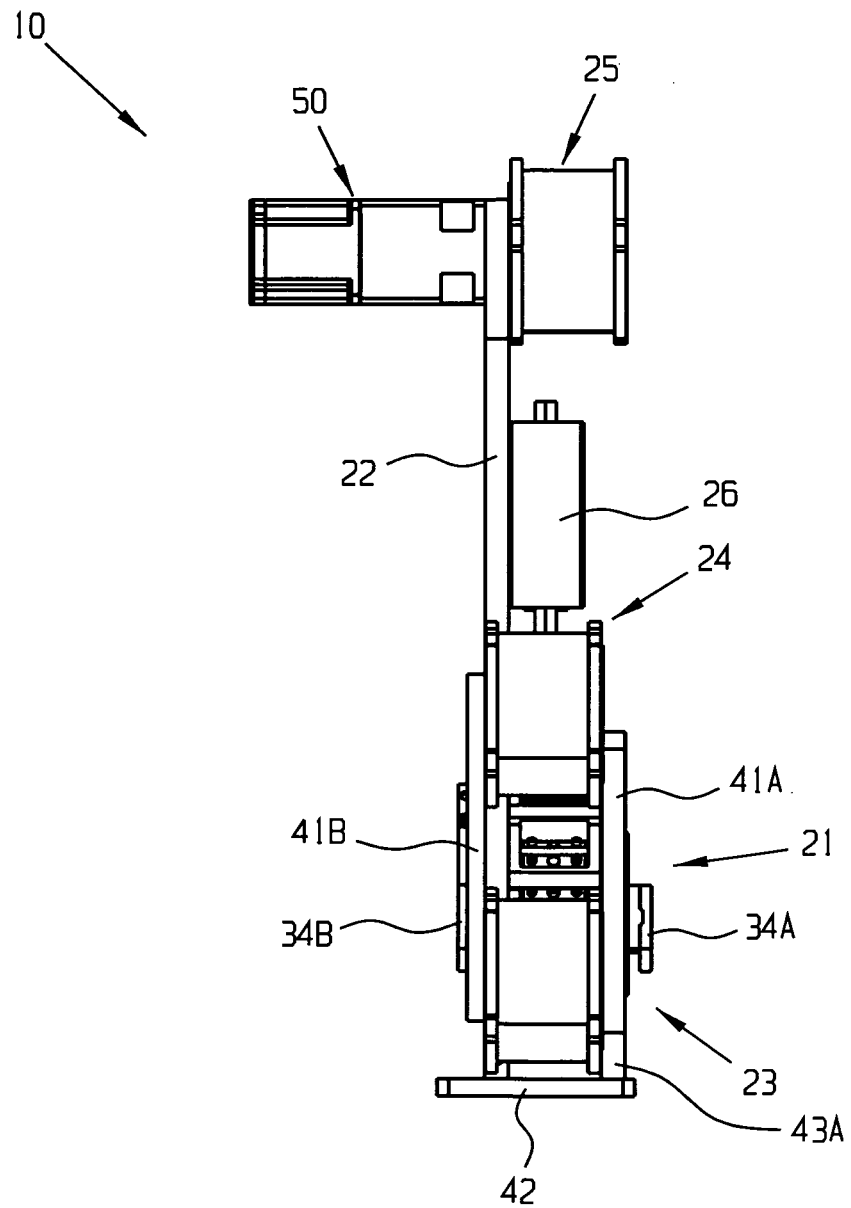
FIG. 9 is a left side view of the apparatus.
Figure 10:
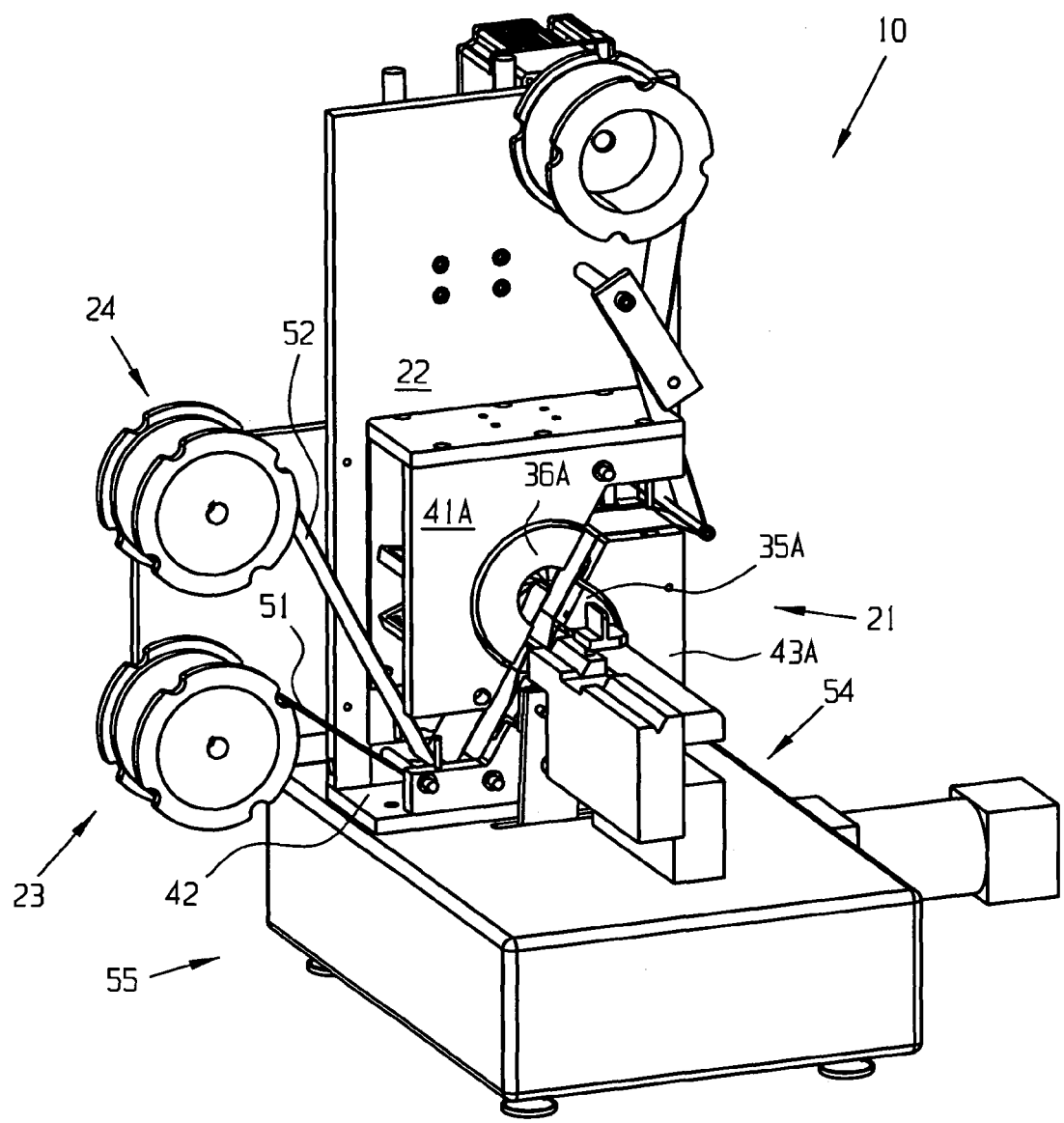
FIG. 10 is a front view of the apparatus with the head opened for film loading.
Figure 11:
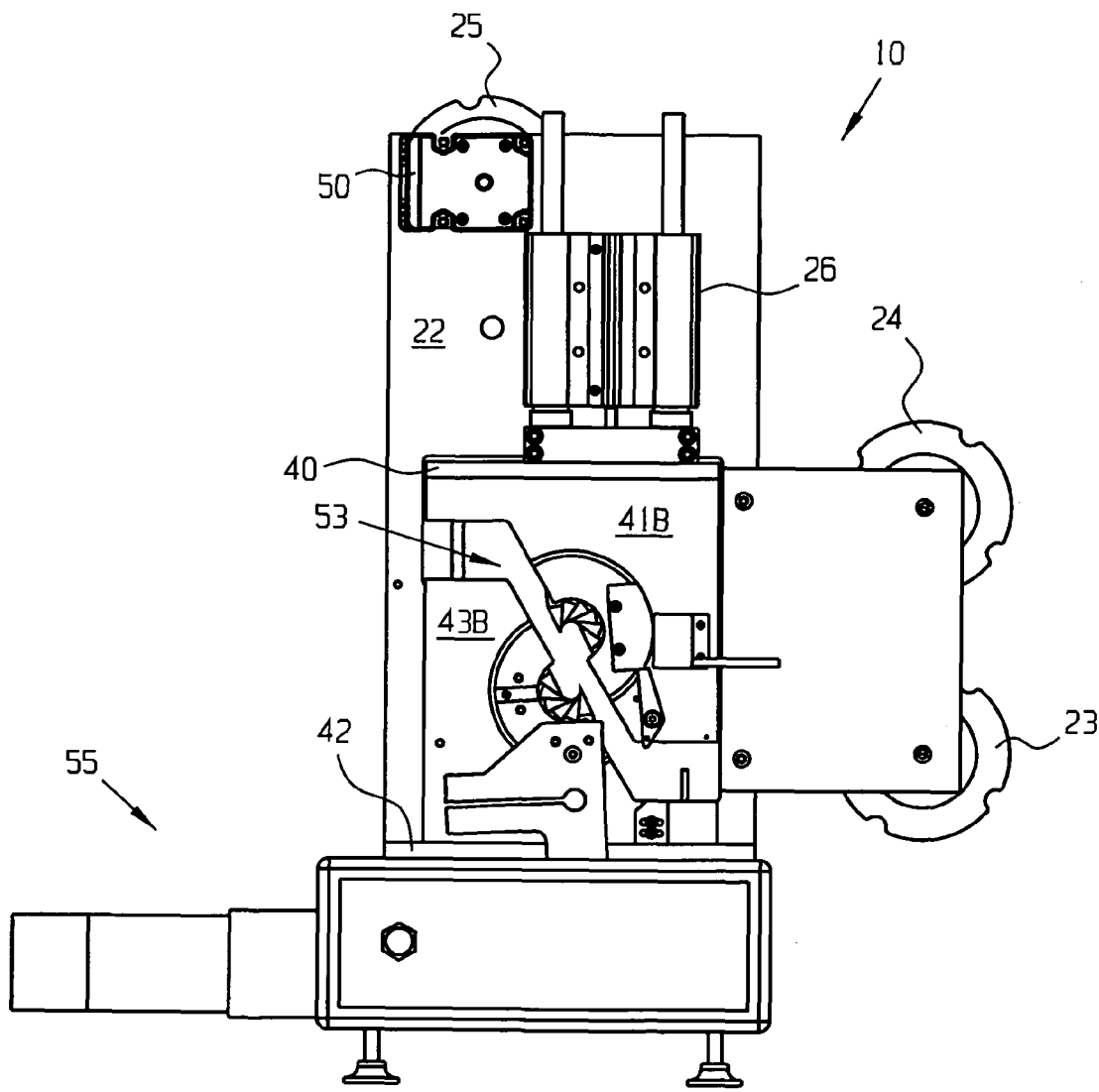
FIG. 11 is a back view thereof.
Figure 12:
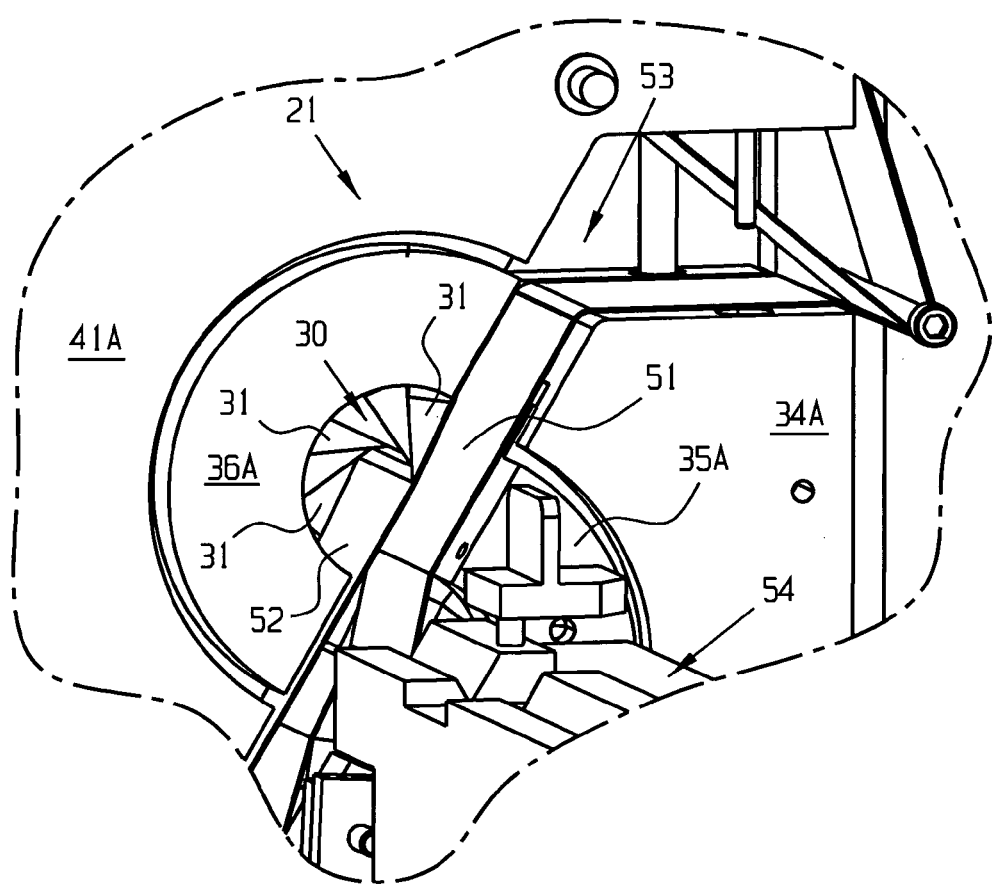
FIG. 12 is a detailed frontal view thereof.
Figure 13:
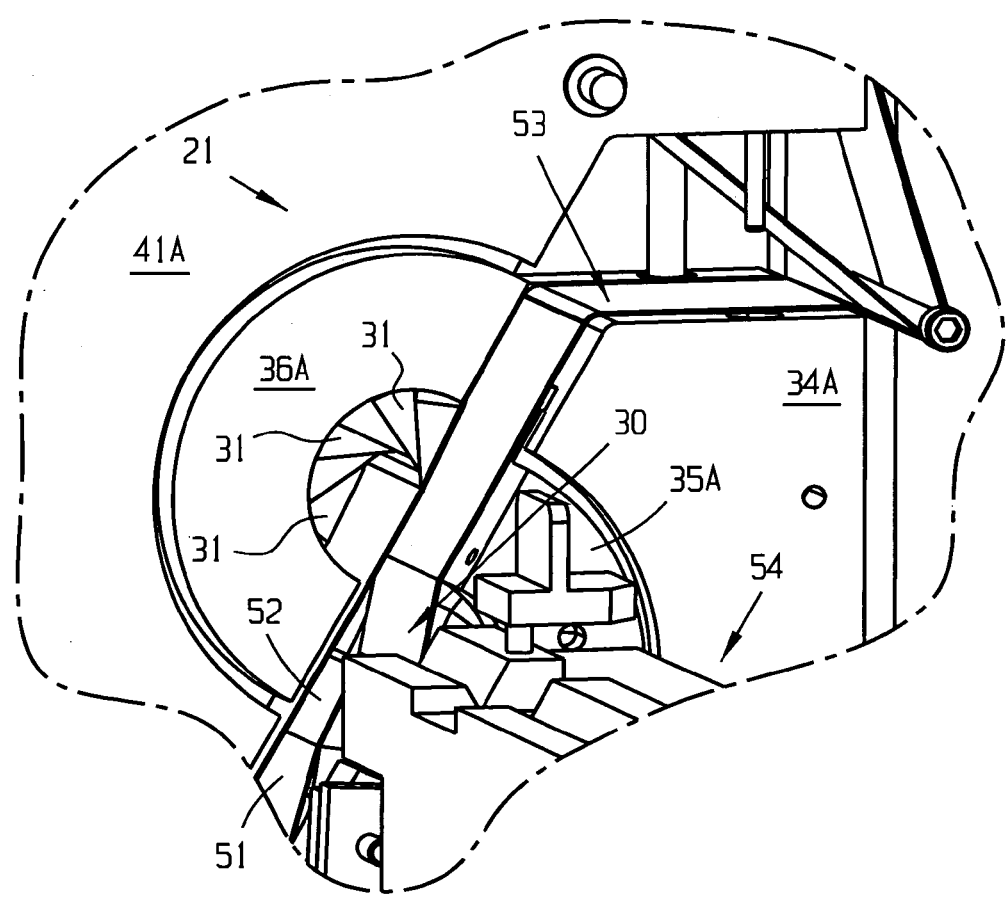
FIG. 13 is a further detailed frontal view thereof.
Figure 14:
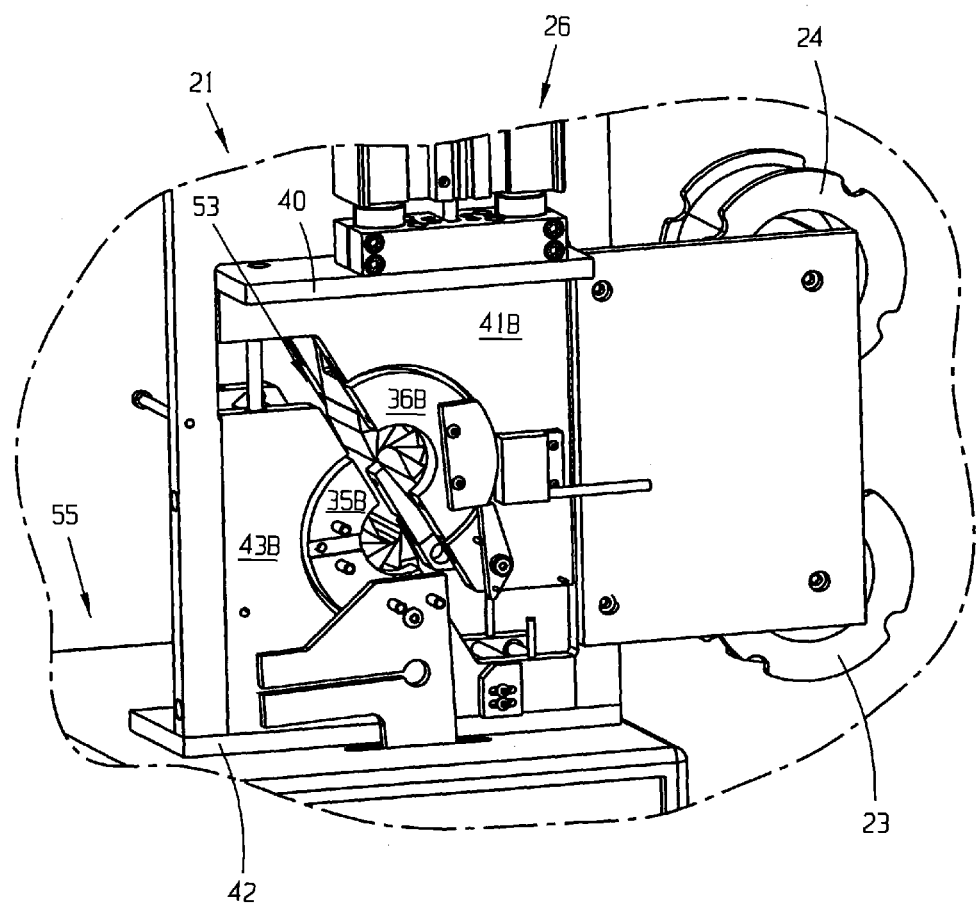
FIG. 14 is a detailed back view thereof.
Figure 15:
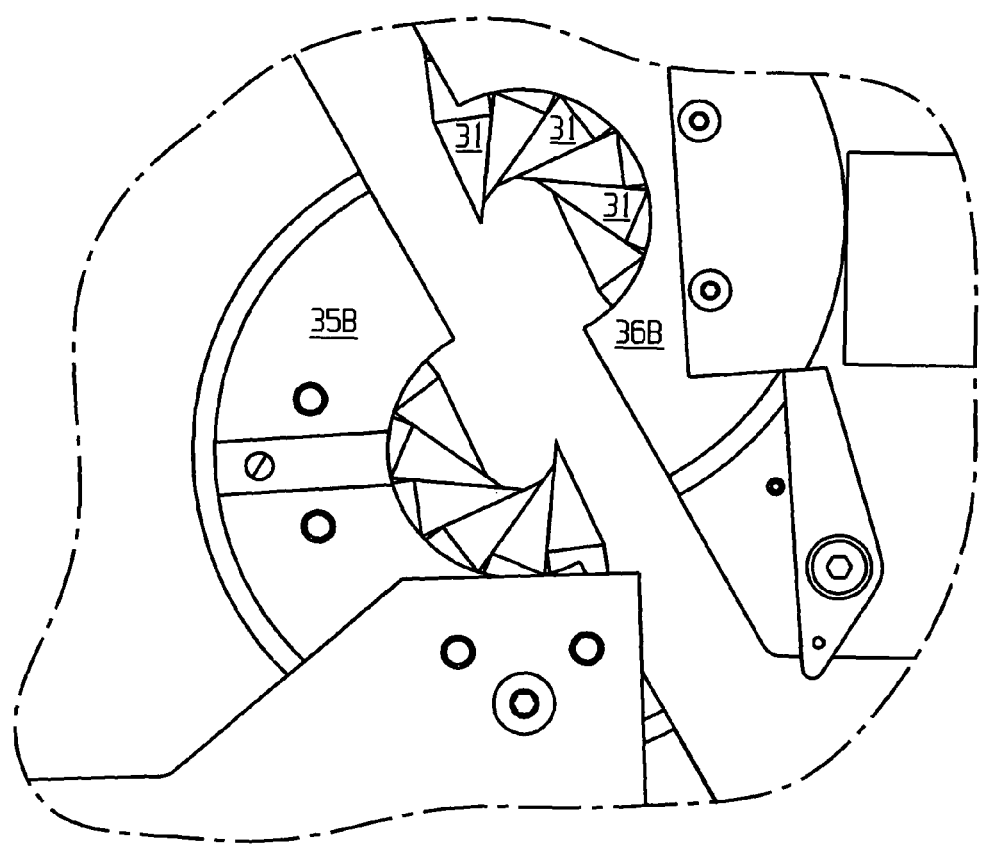
FIG. 15 is a further detailed back view thereof.
Figure 16:
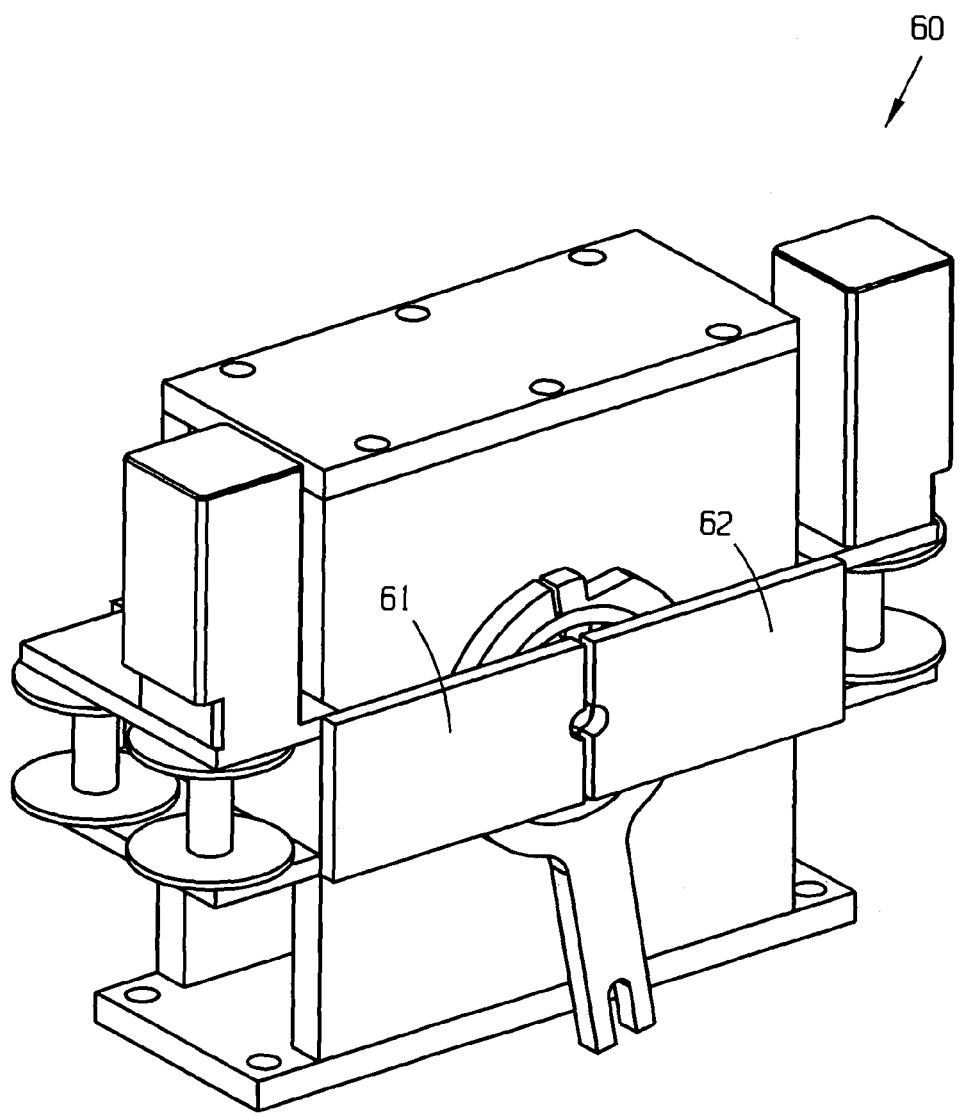
FIG. 16 illustrates an alternative embodiment of the sheathing apparatus.
Figure 17:
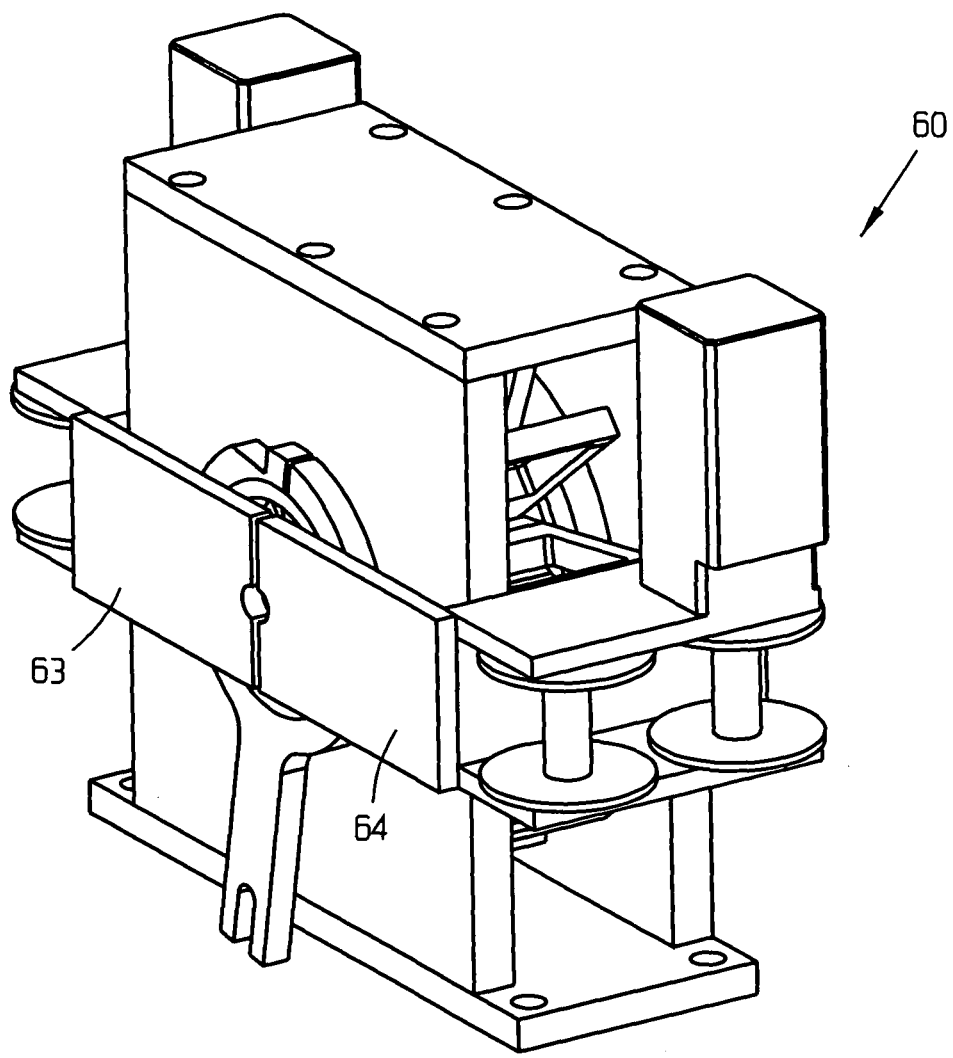
FIG. 17 is a further perspective view thereof.
Figure 18:
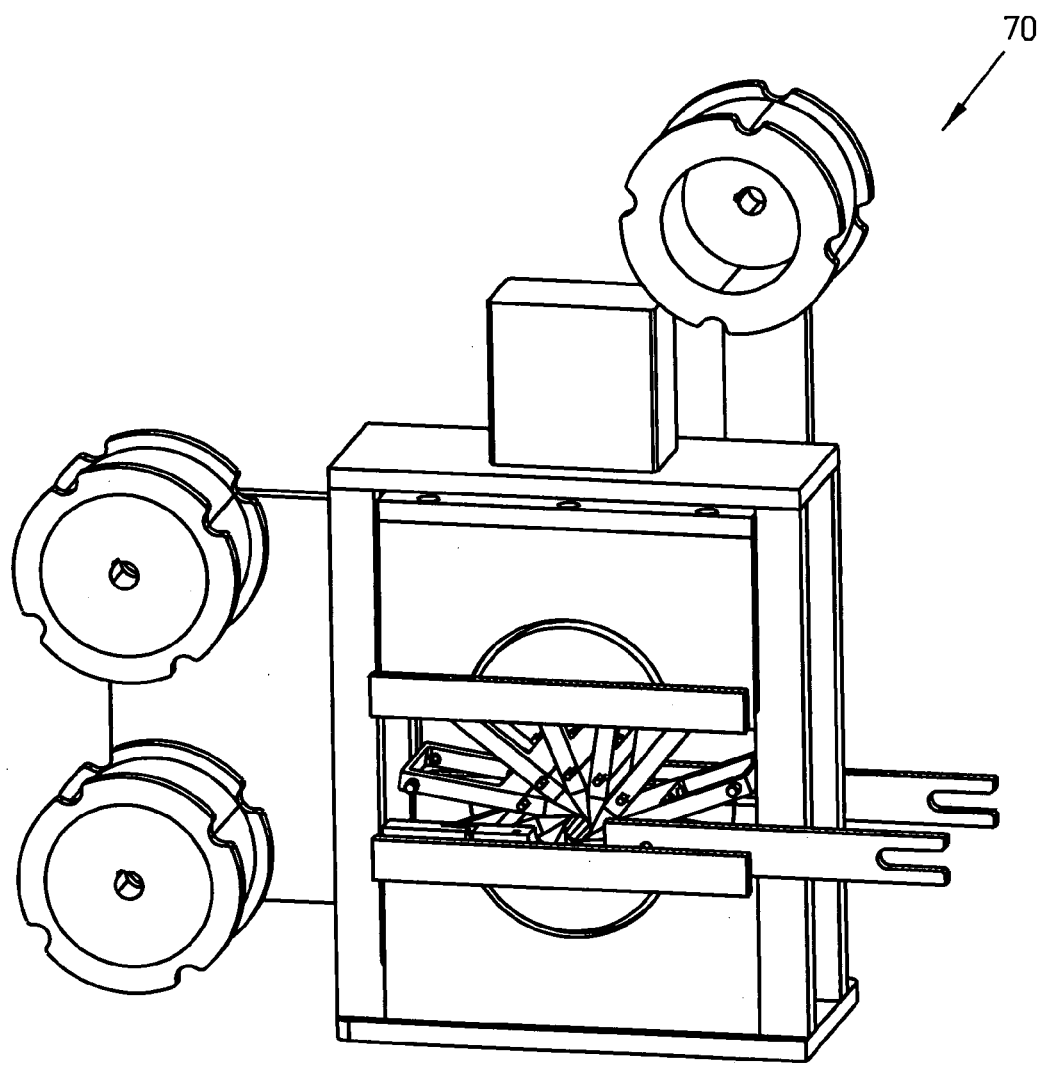
FIG. 18 illustrates another alternative embodiment of the sheathing apparatus, with its head opened.
Figure 19:
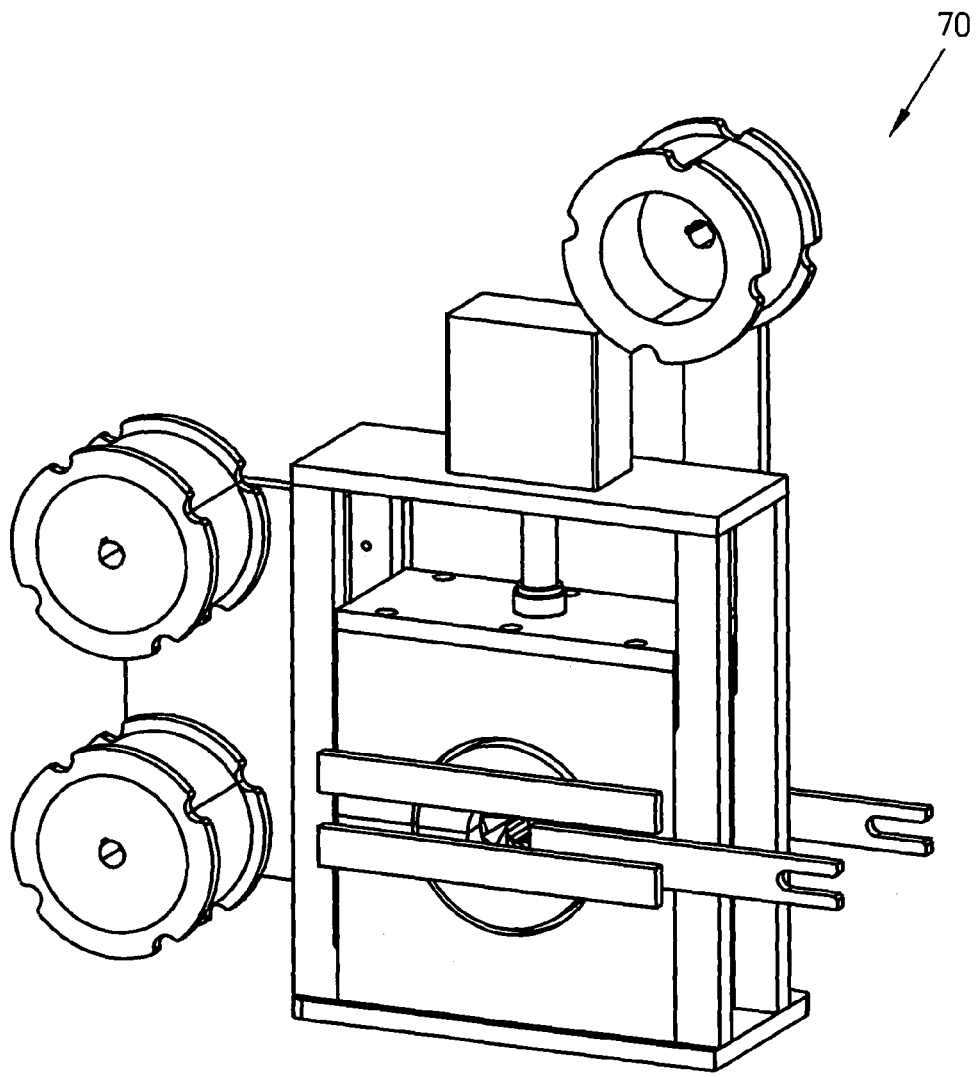
FIG. 19 is a view of the apparatus with its head closed.
Figure 20:
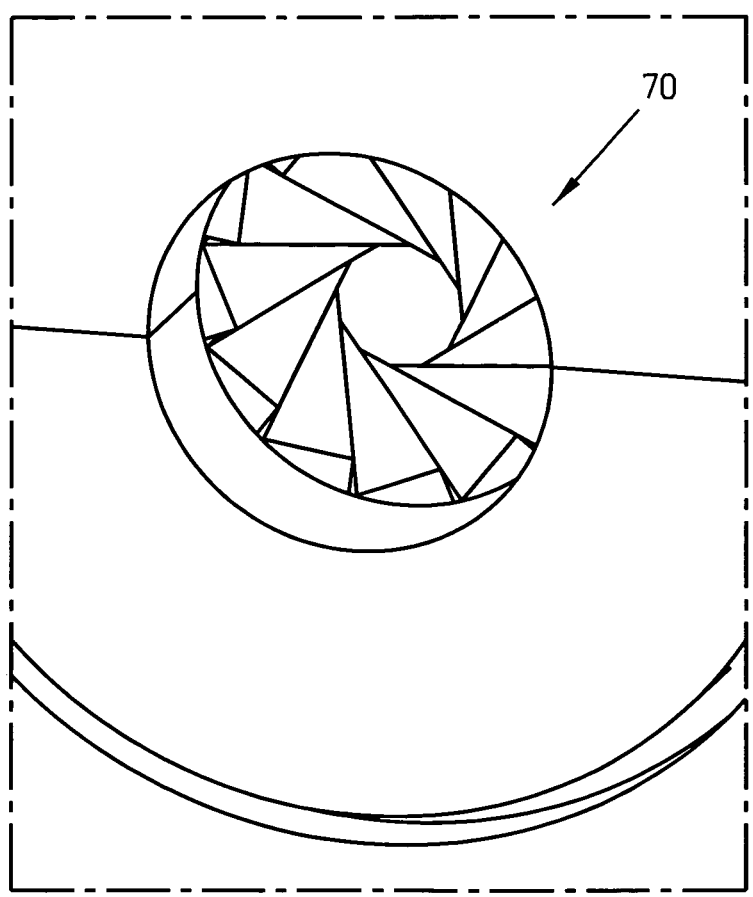
FIG. 20 is a detailed view of the head.

The sheathing process and apparatus of the present invention utilize a pair of flat films of material. No tubular sheath is required as in the prior art. Referring to FIGS. 1 and 2, a sheathed stent assembly 10, comprises a catheter body 11 and a stent 12, with a first or upper 13 and a second or lower 14 flat film, ribbon, or half sheath. The films 13 and 14 are disposed on each side of the stent 12, for example a drug coated stent, also commonly called a drug eluting stent (DES). The films 13 and 14 are preferably automatically fed into one side of a crimp head (See later Figures) in continuous paths. The paths pass through and out the crimp head. The sheaths 13 and 14 protect the stent 12 during a crimping process. The continuous paths eliminate the need to manually handle the stent/catheter assembly 10 in order to place a sheath. Film material, preferably flat, and in a continuous or endless roll or web is lower cost than individual tubular sheaths. Film material is also available in thinner sizes, which improves process control.

A preferred, general embodiment of the method of sheathing a stent 12 comprises the steps of providing a stent assembly including a catheter member 11 and a stent member 12 disposed about the catheter member 11; placing a first sheath film 13 adjacent one side of the stent assembly 11/12; placing a second sheath film 14 adjacent an opposite side of the stent assembly 11/12; and compressing, for example by crimping, the stent assembly 11/12, whereby the first and second sheath films 13 and 14 move toward each other and substantially surround the stent assembly as the stent 12 is crimped to the catheter member 11.

FIGS. 3-9 show an embodiment of the integrated film crimping apparatus 20 of the present invention for sheathing and crimping a sent to a catheter. The apparatus 20 generally comprises a crimper 21, a mounting frame 22 connected to the crimper 21, a lower film roll or payoff 23 and an upper film roll 24 both connected to the frame 22, a take up spool 25 connected to mount 22, and a separation system 26 also connected to the mount 22 and the crimper 21.

The crimper 21 preferably functions generally as a segmental radial compression system as described in U.S. Pat. No. 6,629,350 to Motsenbocker entitled Stent Crimping Apparatus and Method. However, the crimper 21 is constructed and arranged to split or open to permit film to pass through it's central aperture to thereby surround and sheath a stent and catheter operatively placed for crimping. The crimper 21 comprises a pair of crimp head members 32 and 33. Each member 32 and 33 comprises a plurality of segments or elements 31. The elements are preferably movably connected to a distal hub assembly 35/36-, which is connected to an actuation arm 34. The actuation arm 34 may be disposed on both sides of the apparatus 10 or on one side. Other actuation means are useable.

Top member 32 also comprises a top proximal pin plate assembly 41 connected to a top plate 40. Bottom member 33 comprises a bottom proximal pin plate assembly 43 connected to a bottom plate 42.

Separation cylinder assembly 26 preferably comprises cylinders which are mounted to the mount 22 and to the top plate. Take up spool 25 is driven, preferably by motor 50 and pulls film from the payoffs 24 and 23 through the crimper 21.

FIGS. 10-15 show the head in an open position with lower and upper film 51 and 52 passing through slot 53.

Figure 21:
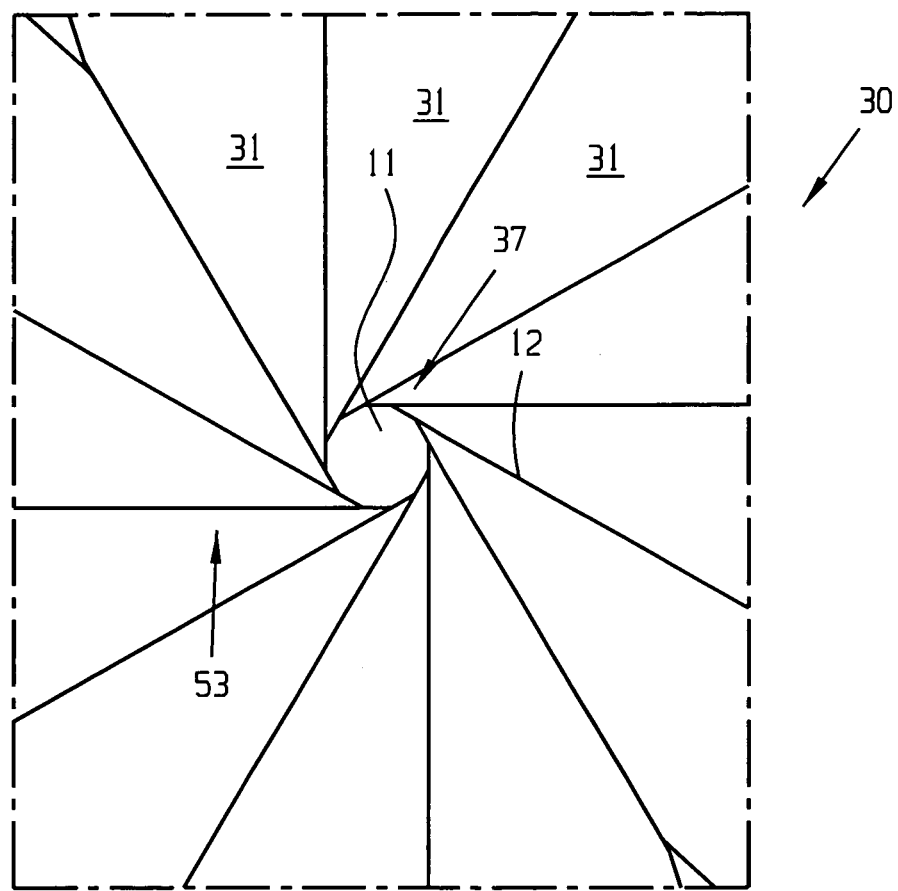
FIG. 21 is a still further detailed view of the head sheathing and crimping a stent on a catheter.

In use, the head 30 is opened by actuating the separation cylinder 26 to separate the member 32 and 33, film is pulled from the payoffs 23 and 24 over the gap between the members 32 and 33 and up to the takeup spool 25. The head 30 is closed by actuating the separation cylinder to bring the members 32 and 33 together. A stent is preferably relatively loosely placed on a catheter. The stent catheter assembly 10 is placed on an input assembly 54, and thereafter loaded in the crimp head 30 central aperture 37, which is open a predetermined amount. In this configuration, the upper and lower films surround the stent/catheter assembly 10. Referring to FIG. 21, the crimper 30 is actuated to segmentally radially compress and crimp the stent onto the catheter. The crimper 30 releases to permit removal of the crimped stent, and the takeup spool actuates to pull a fresh segment of upper and lower film into the crimp aperture. The apparatus 10 is preferably controlled by an electronic control mechanism 55.

FIGS. 16 and 17 and FIGS. 18-20 show an alternative embodiments 60 and 70 of the integrated film crimper for sheathing and crimping that show the film feed-in and take-up modifications. The apparatus 60 for sheathing a stent, also comprises a crimping mechanism; a sheath film supply; a film feeder for moving at least one film from the film supply through the crimping mechanism, and a stent input system for moving a stent assembly into the crimping mechanism. The sheath film may comprises a single film which is folded to substantially surround the stent assembly or a pair of films which are moved together to substantially surround the stent assembly. Folding or moving the film(s) preferably occurs during actuation of the crimping mechanism.

The shape of the upper and lower sheath halves are formed by the guide plates 61-64 illustrated in the crimp head. The two halves are compressed by the crimping and sheathing head to form a tube like structure which substantially completely sheaths the stent assembly during crimping of the stent on to the catheter. The "wings" of the sheath films pass through gaps between the crimp head segments.

Again, thin films of sheath material are stored on the front spools and are feed over the guide plates, through the crimp head and over of the guide plates on the opposite side of the head. The film is then collected on take up spools on the opposite side of the crimp head. The film paths are continuous, which eliminates the need to handle sheath material except for initial loading of the machine. Several thousand stents can be sheathed and processed with one spool of sheath material.

Sheathing protects the drug coating on the stent, or sensitive non-drug coated stents from handling errors. Sheathing also protects the drug coating from wiping or shear during the process of crimping the stent on a delivery or other catheter. Automatic film sheathing eliminates or minimizes costly manual processing, and damage due to misalignment, cross contamination. Such sheathing also ensures one time contact with stents.

Figure 22:
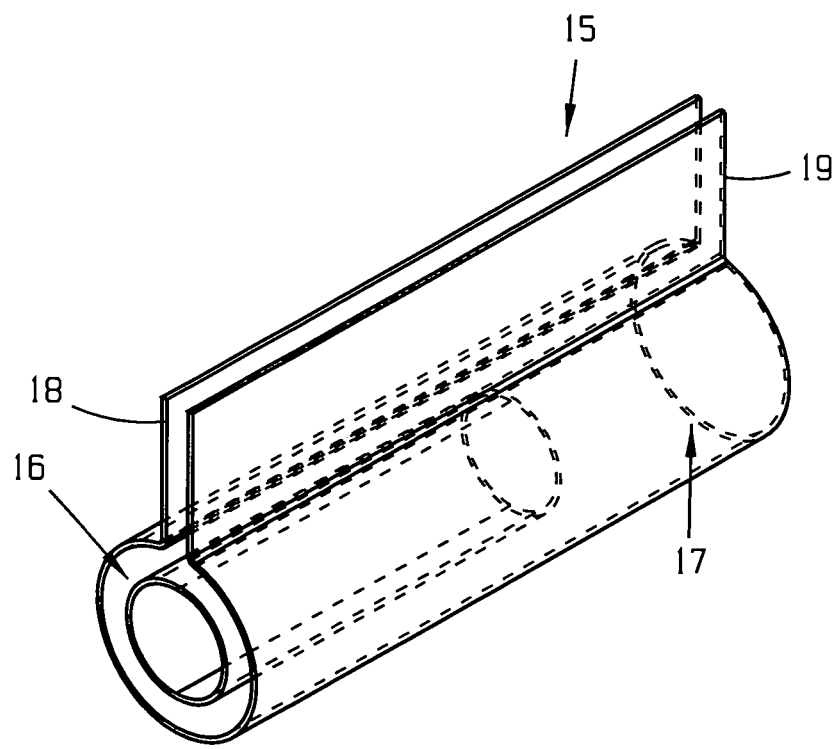
FIG. 22 illustrates another embodiment of the sheath assembly and sheathing method of the invention, including a stent assembly with a single film sheath.
Figure 23:
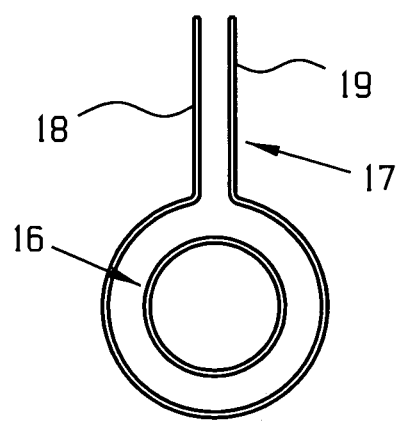
FIG. 23 is an end view thereof.

Referring to FIGS. 22 and 23, another approach to the film sheath assembly 15 is to use a single film 17 formed into a "keyhole" form. The stent 16 protection and "wing" treatment is substantially the same as the double film version. In this alternative embodiment of the method, the steps of the invention comprise providing a stent 16 assembly; placing a first sheath film 17 having a first edge and a second edge adjacent the stent assembly in a predetermined configuration; and compressing the stent assembly, whereby the sheath film surrounds the stent.

The descriptions above and the accompanying drawings should be interpreted in the illustrative and not the limited sense. While the invention has been disclosed in connection with an embodiment or embodiments thereof, it should be understood by those skilled in the art that there may be other embodiments which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

The invention claimed is:

1. An apparatus for sheathing a stent, comprising:
   (a) a compressing mechanism, the compressing mechanism being a segmental radial compressing mechanism comprising a plurality of segments defining a central compression aperture having a longitudinal axis, the compressing mechanism being configured and adapted to split open laterally to permit passage of sheath film;
   (b) a sheath film supply;
   (c) a film feeder for moving at least one sheath film from the film supply through the compressing mechanism, and
   (d) a stent input system for moving a stent assembly into the compressing mechanism.

2. The apparatus of claim 1, wherein the sheath film comprises a single film which is folded by the compressing mechanism to substantially surround the stent assembly.

3. The apparatus of claim 1, wherein a pair of films are moved together by the compressing mechanism to substantially surround the stent assembly.

4. The apparatus of claim 1, wherein the at least one sheath film is moved through the compressing mechanism in synchronization with moving a stent assembly into the compressing mechanism.

5. The apparatus of claim 1, wherein the compressing mechanism crimps a stent of the stent assembly onto a catheter of the stent assembly at the same time the at least one sheath film substantially surrounds the stent assembly.

6. The apparatus of claim 1, wherein the sheath film supply comprises at least one roll.

7. The apparatus of claim 6, wherein the sheath film supply comprises two rolls of sheath film.

8. The apparatus of claim 6, wherein the sheath film supply feeds sheath film in a continuous path from at least one roll.

9. The apparatus of claim 1, wherein sheath film passes laterally through the compressing mechanism and into the compression aperture.

10. The apparatus of claim 9, wherein the sheath film supply is disposed to a lateral side of the compressing mechanism.

* * * * *